US006909912B2

(12) United States Patent
Melker (10) Patent No.: US 6,909,912 B2
(45) Date of Patent: Jun. 21, 2005

(54) NON-INVASIVE PERFUSION MONITOR AND SYSTEM, SPECIALLY CONFIGURED OXIMETER PROBES, METHODS OF USING SAME, AND COVERS FOR PROBES

(75) Inventor: Richard Melker, Gainesville, FL (US)

(73) Assignees: University of Florida, Gainesville, FL (US); Beta Biomed, Inc., Rowlett, TX (US)

( * ) Notice: Subject to any disclaimer, the term of this patent is extended or adjusted under 35 U.S.C. 154(b) by 300 days.

(21) Appl. No.: 10/176,310

(22) Filed: Jun. 20, 2002

(65) Prior Publication Data

US 2003/0236452 A1 Dec. 25, 2003

(51) Int. Cl.[7] .................................................. A61B 5/00
(52) U.S. Cl. ...................................... 600/323; 600/324
(58) Field of Search ................................. 600/322–323, 600/324

(56) References Cited

U.S. PATENT DOCUMENTS

| 5,218,962 | A  |   | 6/1993  | Mannheimer et al. |         |
|-----------|----|---|---------|-------------------|---------|
| 5,309,908 | A  | * | 5/1994  | Friedman et al.   | 600/322 |
| 5,743,857 | A  | * | 4/1998  | Shinoda et al.    | 600/494 |
| 5,788,634 | A  | * | 8/1998  | Suda et al.       | 600/382 |
| 6,263,223 | B1 |   | 7/2001  | Shepherd et al.   |         |
| 6,334,065 | B1 |   | 12/2001 | Al-Ali et al.     |         |

FOREIGN PATENT DOCUMENTS

| WO | WO 00/21435 A1 | 4/2000 |
| WO | WO 01/54575 A1 | 8/2001 |
| WO | WO 01/62194 A1 | 8/2001 |

OTHER PUBLICATIONS

US 4,928,691, 5/1990, Nicolson et al. (withdrawn)
James E. Sinex, MD. Pulse Oximetry: Principles and Limitations. American Journal of Emergency Medicine. vol. 17. No. 1. pp. 59–66. Jan. 1999.
ECRI A Nonprofit Agency, In–line Blood/Solution Warmers. Health Devices, vol. 25, No. 10, p. 370. Oct. 1996.
Mallinckrodt, Inc., Nellcor Sensor Selection Guide. 1999.
Wedel C., Ve Scharf, MWM Stratling, H. Sulf, A. Petry, Abstract No. A20: Development of a Method of Pulse Oximetry at the Nasal Septum, STA–ISIAPO. S110.
VSM Medtech Ltd., Optical Sensing, Continuous Non–Invasive Blood Pressure Monitor, http://www.vsmmedtech.com/Technology/beat_2_beatB.htm.
Prof. Dr. J. Schwider, Multiwavelength pulse oximeter, http://www.optik.uni erlangen.de/mikos/projects/Pulsoximeter/POXI.HTM, Aug. 1998.

\* cited by examiner

*Primary Examiner*—Eric F. Winakur
*Assistant Examiner*—Matthew Kremer
(74) *Attorney, Agent, or Firm*—Timothy H. Van Dyke; Joseph Fischer; Beusse Brownlee Wolter Mora & Maire (57) ABSTRACT

The present invention relates to a novel non-invasive perfusion/resistance status monitor system and methods of using the same, and more specifically, a vascular perfusion status monitor system receiving and processing signals from at least two pulse oximeter probes, where each of the at least two pulse oximeter probes are situated at advantageously different locations in a patient. Novel pulse oximeter probes are configured to be placed, respectively, across the lip or cheek, across the septum or nares of the nose, and on the tongue. These probes are fabricated to provide signals to estimate arterial oxygen saturation. Conventional oximeter probes also can be configured to function according to the novel methods of determining differences in peripheral blood flow and/or resistance described herein.

12 Claims, 6 Drawing Sheets

NON-INVASIVE PERFUSION MONITOR AND SYSTEM, SPECIALLY CONFIGURED OXIMETER PROBES, METHODS OF USING SAME, AND COVERS FOR PROBES

FIELD OF THE INVENTION

The present invention relates to the field of non-invasive measurement of signals indicating arterial blood oxygen saturation by means of pulse oximetry. Such measurements are made at two or more advantageously identified sites to provide additional information regarding the state of peripheral perfusion and resistance in a patient. Novel configurations of probes for detection of signals are also disclosed.

BACKGROUND OF THE INVENTION

Diseases, acute injuries, and other conditions can adversely affect blood flow to and in the limbs. In a general sense, agents and factors that may affect and lower circulation to the limbs, also known as peripheral circulation, include certain drugs, especially vasoconstrictors, poor perfusion per se due to shock, such as results from low blood volume, or septic or cardiogenic shock, certain traumas, external pressure (as from burns), hypothermia, and other mechanical abnormalities or injuries. In particular, decreased peripheral circulation may be caused by a number of disorders within the body including, but not limited to, atherosclerosis, Raynaud's disease, Buerger's disease, chronic obstructive pulmonary diseases (COPD), and embolic occlusive disease.

Poor blood flow reduces the amount of oxygen that is carried in the blood stream to cells. Emergency rooms, intensive care units, burn units, operating rooms, and ambulances treat a variety of critically ill patients in need of continuous monitoring of real time hemoglobin saturation and/or blood pressure readings. If oxygen levels in the blood become very low at peripheral sites, a variety of problems may occur which include inadequate resuscitation, cell death or necrosis that can lead to non-healing lesions, gangrene and amputation of limbs. Also, in progressive diabetes and other conditions that may result in atherosclerosis that affect peripheral circulation and perfusion, non-invasive measurement of circulation and/or resistance status is useful to monitor the progression of the disease and the effectiveness of treatments.

Blood oxygen levels are currently measured by pulse oximetry, which can be divided into transmittance and reflectance types. Transmittance, or transillumination oximetry, involves the process whereby a sensor measures light extinction as light passes through a portion of blood-perfused tissue. Light is transmitted from one side of a portion of blood-perfused tissue, and is recorded by a sensor situated across the portion of tissue. Reflectance oximetry, on the other hand, has both the light source and the sensor on one side of the tissue, and measures reflectance back from the tissue. For both types of oximetry, multiple signals from the light sensor, or detector, are used to estimate the oxygen saturation and pulse rate from changes in absorption of the light detected throughout blood pulse cycles. The technology is based on the differential absorbence of different wavelengths of light by different species of hemoglobin.

Conventional pulse oximetry measurement in certain classes of patients, for instance severely burned patients, can be a significant challenge, yet this monitoring data is vital in operating room and intensive care settings. Most current pulse oximetric approaches depend upon available peripheral sites permitting transillumination oximetry which is sufficient for most surgical conditions and procedures. However, in one example, patients with severe burns often have only a few sites suitable for the effective placement of the transmitting pulse oximeter sensor. These patients often have severe circulatory compromise rendering the current peripheral pulse oximeters less effective.

The technology of pulse oximeters is well known (See "Pulse Oximetry: Principles and Limitations," J. E. Sinex, Am. J. Emerg. Med., 1999, 17:59–66). Pulse oximetry includes a sensor, or probe, with light source(s) generating at least two different wavelengths of light, and a detector placed across a section of vascularized tissue such as on a finger, toe, or ear lobe. Pulse oximetry relies on the differential absorbence of the electromagnetic spectrum by different species of hemoglobin. In a typical system, two distinct wavelength bands, for instance 650–670 nm and 880–940 nm, are used to detect the relative concentrations of oxygenated hemoglobin (oxyhemoglobin) and non-oxygenated reduced hemoglobin, respectively. The background absorbence of tissues and venous blood absorbs, scatters and otherwise interferes with the absorbence directly attributable to the arterial blood. However, due to the enlargement of the cross-sectional area of the arterial vessels during the surge of blood from ventricular contraction, a relatively larger signal can be attributed to the absorbence of arterial hemoglobin during the systole.

By averaging multiple readings and determining the ratio peaks of specific wavelengths, a software program can estimate the relative absorbence due to the arterial blood flow. First, by calculating the differences in absorption signals over short periods of time during which the systole and diastole are detected, the peak net absorbence by oxygenated hemoglobin is established. The signals typically are in the hundreds per second. The software subtracts the major "noise" components (from non-arterial sources) from the peak signals to arrive at the relative contribution from the arterial pulse. As appropriate, an algorithm system may average readings, remove outliers, and/or increase or decrease the light intensity to obtain a result. The results from one site provide a measurement of arterial oxygen saturation at that site, and also allows calculation of the shape of the pulse at the placement site of the probe, which can be developed into a plethysymograph. Among the various sources of signal interference and modification, it is noted that the shape of red blood cells changes during passage through arterial and venous vessels. This change in shape affects scattering of the light used in pulse oximetry. Algorithms are designed to correct for such scattering.

More sophisticated pulse oximetry systems detect at more than merely two bands, such as the 650–670 nm and 880–940 nm wavelength bands. For instance, the pulse oximetry article from a uni-erlangen web site stated that four LEDs, at 630, 680, 730 and 780 nm, each with 10 nm bandwidths, can determine the four common species of hemoglobin. The article further calculated that the detection of nine wavelengths in the range of 600 to 850 nm would provide greater accuracy in assessing these four forms of hemoglobin, oxyhemoglobin ($O_2Hb$), reduced hemoglobin (HHb), methemoglobin (MetHb), and carboxyhemoglobin (COHb). As used in the present invention, the term "pulse oximeter" or "oximeter" is meant to include all designs and types of pulse oximeters, including current and later developed models that transmit and detect at more than two wavelengths associated with absorption differences of these hemoglobin species.

At present, peripheral vascular resistance can only be measured invasively, or non-invasively by skilled technicians using Doppler flow devices. The use of Doppler and Doppler waveform analysis is now a standard investigation technique for obtaining measurements in blood flow resistance patients with possible circulatory disorders. For example, Dougherty and Lowry (J. Med. Eng. Technol., 1992: 16:123–128) combined a reflectance oximeter and a laser Doppler flowmeter to continuously measure both blood oxygen saturation and perfusion.

A number of patents have been issued directed to monitors, sensors and probes for use in pulse oximetry procedures. For instance, U.S. Pat. No. 6,334,065, issued on Dec. 25, 2001 to Al-Ali, et al., discloses a stereo pulse oximeter that provides for simultaneous, non-invasive oxygen status and photoplethysmograph measurements at both single and multiple sites. The invention is directed to the detection of neonatal heart abnormalities, particularly related to defects of heart-associated vessels, and specifically directed to Persistent Pulmonary Hypertension in Neonates (PHHN), Patent Ductus Arteriosis (PDA), and Aortic Coarctation. All of these conditions result in a flow of differentially oxygenated blood to different peripheral extremities. For instance, in PHHN and PDA, the blood that flows to the right hand is unaffected by the abnormal shunt that results in less oxygenated blood flowing to other areas. Thus, comparison of oxygen saturation values between a pulse oximeter sensor at the right hand and at, for instance, a foot site, is stated to detect or confirm the diagnosis of such neonatal heart abnormalities. Continuous monitoring with such pulse oximetry also is proposed, to provide feedback on the effectiveness of treatments or surgery to deal with these neonatal cardio/cardiopulmonary conditions. U.S. Pat. No. 6,334,065 does not address the use of two probes for detection, confirmation, or monitoring of perfusion- and resistance-related conditions in the patient. Such conditions would not be expected in a neonatal patient, and are instead more likely found in aging patients and in patients with certain accident conditions unrelated to neonatal heart and heart-associated vessel anomalies.

U.S. Pat. No. 6,263,223 was issued on Jul. 17, 2001 to Shepard et al., and teaches a method for taking reflectance oximeter readings within the nasal cavity and oral cavity and down through the posterior pharynx. Whereas the conventional transillumination pulse oximeter probe detects the light not absorbed or scattered as it crosses a vascularized tissue covered by skin (i.e., the LEDs and photodetector are separated by the tissue), a reflectance oximeter probe detects light by backscattering of light that traverses vascularized tissue not bounded by skin and is reflected back to a detector positioned on the same side of the tissue as the LEDs (e.g., on tissue in the mouth). The method includes inserting a reflectance pulse oximeter sensor into a cavity within a subject's skull and contacting a capillary bed disposed in the cavity with the reflectance pulse oximeter sensor. The method uses standard pulse oximeter sensor probes placed over capillary beds close to a buccal surface, posterior soft palate, hard palate or proximal posterior pharynx, including the tongue, nares or cheek. Reflectance pulse oximetry at these sites determines arterial oxygen saturation. One major problem with this device is that it does not permit cross-site comparisons of oxygen saturation values between several tissue sites. In addition, the pulse oximeter device used in this invention is an elongated tube that is inserted far into the nasal or oral cavity down into the pharynx, which is a highly invasive procedure.

U.S. Pat. No. 4,928,691, issued on May 29, 1990 to Nicolson et al., and currently withdrawn, discloses a non-invasive, electro-optical sensor probe and a method for its use. The sensor is enabled to measure light extinction during transillumination of a portion of blood-perfused tissue and to calculate the oxygen saturation and pulse rate from changes in absorption of the light detected. The sensor probe is placed at a central site such as the tongue, cheek, gum or lip of the patient and provides continuous assessment of arterial oxygen saturation and pulse rate. The sensor is malleable and extremely flexible, and is stated to conform to the structure of the skin and underlying tissue. U.S. Pat. No. 4,928,691 states that measurement at the preferred central sites provide accurate oxygen saturation and pulse readings for "patients with lowered or inconsistent peripheral perfusion." Critically, the probes according to U.S. Pat. No. 4,928,691 are highly flexible, leading to a high likelihood that upon typical movement of the patient there would be mal-alignment between the light source(s) and sensor, resulting in skewed, non-usable, or unreliable signals and results. Also, there is no teaching or suggestion to compare oxygen saturation values between several tissue sites to identify, characterize, or monitor peripheral perfusion conditions in such patients.

U.S. Pat. No. 5,218,962 was issued on Jun. 15, 1993 to Mannheimer et al., teaches a pulse oximetry system which monitors oxygen saturation and pulse rates by sensing the blood characteristics at two or more peripheral sites. The device includes one or more pulse oximetry probes which passes light through unique regions of tissue and a sensor which detects the amount of light passing through the tissue, and an instrument that independently calculates oxygen saturation level within each region. The difference in values represents how much the oxygen saturation of the first region of tissue differs from the oxygen saturation of the second region of tissue. When the difference between the two values is below a set threshold, the '962 patent attributes this to a sufficiently high probability that the value is true, and displays an oxygen saturation value that is a function of the two independent values. Where there is a difference greater than a set threshold, no oxygen saturation value is displayed. Thus, the '962 patent attributes substantial differences between two sites to be due to error, rather than to an indication of a problem with peripheral perfusion and/or resistance.

WIPO Application No. WO0021435A1, to Barnett et al., was published Apr. 20, 2000. This publication teaches a non-invasive spectrophotometric examination and monitoring of blood metabolites in multiple tissue regions on an ongoing and instantaneous basis. The method includes attaching multiple sensors to a patient and coupling each sensor to a control and processing station enabled to analyze signals conveyed thereto. The control and processing station visually displays the data from multiple sites for direct mutual comparison of oxygen saturation values from multiple sites. A key aspect of the invention is the use of a "near" and a "far" (or "deep") detector at each detection site. Based on the positioning of the light-generating devices and the near and far sensors, the far sensor receives absorption signals from deeper inside the brain tissue. In a basic configuration, the "near" sensor, or detector, principally receives light from the source whose mean path length is primarily confined to the layers of skin, tissue, and skull, while the "far" detector which receives light sprectra that have followed a longer mean path length and traversed a substantial amount of brain tissue in addition to the bone and tissue traversed by the "near" detector. Other configurations indicate receptors receive signals from sources across the entire brain cross-section. This is stated to provide information about, by calculation differences, the condition of the deeper tissue, in particular the brain. The method is directed to compare oxygen saturation values for cerebral tissue, such as comparing the two hemispheres during surgery. The WO0021435A1 invention distinguishes itself from standard pulse oximetry of arteries close to the surface of the body, and focuses primarily on analysis of deeper tissues and organs. The application does not teach a method to measure "surface" peripheral or central tissue sites for development of information regarding perfusion status.

WIPO Application No. WO0154575A1, to Chen et al., was published on Aug. 2, 2001. This publication teaches a non-invasive apparatus and method for monitoring the blood pressure of a subject. A monitor is used for continuous, non-invasive blood pressure monitoring. The method includes using sensors to detect a first blood pressure pulse signal at a first location on patient and detecting a second blood pressure pulse signal at a second location on the patient; measuring a time difference between corresponding points on the first and second blood pressure pulse signals; and, computing an estimated blood pressure from the time difference. The first and second sensors are placed at locations such as a finger, toe, wrist, earlobe, ankle, nose, lip, or any other part of the body where blood vessels are close to the surface of the skin of a patient where a blood pressure pulse wave can be readily detected by the sensors, and/or where a pressure pulse wave from the patient's heart takes a different amount of time to propagate to the first location than to the second location.

A superior monitor system would be able to provide real-time continuous measurements of signals that would be analyzed to provide arterial oxygen saturation, blood pressure, and pulse rate. A superior monitor system would utilize at least two pulse oximeter probes, one of which is placed at a highly perfused central tissue, such as the lip, tongue, nares, cheek, and a second probe placed at a typically less perfused areas such as a finger or toe. Also, in some situations, a peripheral probe may be placed at sites in or distal from areas that may be or are affected by disease- or accident-related diminished blood perfusion to tissues.

All patents, patent applications and publications discussed or cited herein are incorporated by reference to the same extent as if each individual publication or patent application was specifically and individually set forth in its entirety.

SUMMARY OF THE INVENTION

One aspect of the present invention relates to a novel non-invasive vascular perfusion/resistance monitor system having at least two pulse oximeter probes positioned at locations on the body of a patient, the signals from which may be capable of indicating a problem with peripheral perfusion and/or resistance. In practice each probe emits at least two different light frequencies, such as by light-generating diodes (LEDs), and such emitted light is detected by at least one light detector, such as a photodiode detector. A general-purpose computer or a special purpose computer is employed to perform complex mathematical computations based, typically, on the signal intensity and timing from the at least two pulse oximeter probes, and on signals from the light detectors of each of the probes. Proper analysis by software programming in such general-purpose computer or special purpose computer outputs results to a display, printer, etc. that suggests or indicates (depending on relative differences in the signals at different locations, and upon other conditions) whether a condition of diminished or abnormal vascular perfusion/resistance may exist in a selected body area. The system also monitors changes in such conditions during treatment interventions.

In a preferred embodiment, software programming provides for a signal to a user of the device to alert the user when signals from a central or a non-central probe are of such low pulse amplitude that either the probe needs repositioning or that the patient is experiencing extremely low pulse at the probe site (and is therefore in need of acute intervention). The software program also converts the signals from the light detectors to calculate various oxygen saturation values and various blood pressure values (either simultaneously or separately). These values are used for evaluating the vascular perfusion/resistance and/or blood pressure of a patient based on the locations of the two or more probes.

Each probe is designed for monitoring blood oxygen saturation and/or blood pressure at different vascular bed sites on a patient. Critically, one of the at least two sites on a patient is at what is designated a "central source" site ("CSS"). The inventors have discovered that flow directed through the carotid artery and detected at CSS sites, such as the lip, tongue, nasal nares, and facial cheek, are typically strong and unaffected by perfusion-lowering conditions. In patients who do not have perfusion-lowering conditions, a second or third probe site at "non-central" site (NCS), such as an extremity (i.e., fingers, toes, etc.), provides oxygen saturation and pulse values fairly comparable to values from the CSS. However, when a patient has a perfusion-lowering condition, the probe site at an affected extremity provides noticeably different oxygen saturation and pulse values compared to the CSS values. The difference in saturation values between the CSS and one or more sites is then used to assess peripheral vascular resistance, perfusion and/or peripheral vascular disease.

As used in this disclosure, when a particular wavelength or band of wavelength is stated at which an LED or other light-generating source emits light, it is understood that such light-generating source may and probably does emit light across a broader range. However, what is meant by such statement is that such light-generating source is designed to emit at a frequency curve which has a peak at or near such stated wavelength or band. It is further understood that any known means of limiting non-desired light energy, such as by selective filtration, may be used in conjunction with such light-generating sources to improve the accuracy and/or precision of the emissions of such light-generating sources.

As used in this disclosure, a "pad" is meant to indicate a housing, or an enclosure, over a light-generating or a light-sensing device on the probe, which provides a barrier to fluids, and permits transmission of light of the relevant wavelengths to the present invention. A typical pad has a composition of clear plastic.

As used in this disclosure, a "conductor" is meant to indicate any physical pathway or any system that communicates a signal or electricity from a first to a second location. Signals and electricity can be conducted by conventional means, such as by sending electrical impulses along a continuous copper wire, by more sophisticated means, such as by converting the signals into radio waves and transmitting these waves such that a receiver receives the signals and thereafter sends them to the controller, or by any other way now known or later developed.

While some researchers have attempted to gauge accuracy by comparing the results from two different pulse oximeter probe sites (see U.S. Pat. No. 5,218,962), and other researchers generally recognized that "central" sites are generally more reliable and responsive than "peripheral" sites (see U.S. Pat. Nos. 6,263,223, and 4,928,691), the present invention recognizes the reasons for the inconsistently different results between CSS and non-CSS sites. Specifically, patients having compromised peripheral circulation and/or resistance will tend to have lower peripheral values than patients without such compromised conditions. By such recognition, detection and monitoring impaired peripheral circulation is possible through the present disclosure. The monitoring system of the present invention additionally provides an indication of vascular resistance through continuous monitoring of the transit time difference of the blood oxygen saturation values and the blood pressure values between the two sites.

It is an object of the present invention to provide a monitoring system which includes two pulse oximeter sensors, or probes, connected to a monitor system as a non-invasive means for continuously measuring blood oxygen saturation values and/or blood pressure and/or pulse values, wherein the system detects and monitors changes in vascular perfusion and resistance in a patient. The overall system particularly assesses differences in peripheral blood flow which may be impaired in certain illnesses and accident conditions.

Another object of the present invention is to provide probes functionally constructed to provide more reliable signal reception and transmission for patients, such as those in ICU, surgery, post-operative care, and patients with respiratory, circulatory problems, or under anesthetics. In particular, pulse oximeter probes are configured to be placed, respectively, across the lip or cheek, in the nostrils of the nose, and on the tongue.

Thus, one object of the invention is to provide a novel configuration of an oximeter probe that is well-suited for placement across the lip of the mouth of a patient, or the cheek of a patient, in which one side of the probe is situated outside the oral cavity and a second side is positioned inside the mouth cavity, and the tissue between the two sides is assessed by transillumination pulse oximetry.

Another object of the invention is to provide a novel configuration of an oximeter probe that is well-suited for placement at the nasal cavity of a patient, in which one side of the probe is situated to the left side of the nasal septum, and a second side is positioned to the right side of the nasal septum, and the tissue between the two sides is assessed by transillumination pulse oximetry. This design, in a preferred embodiment, also functions to provide oxygen to the patient through channels provided in the structure of the probe.

Another object of the invention is to provide a novel configuration of an oximeter probe that is well-suited for placement on both sides of either the right or the left nasal alar (i.e., the alar nari). One side of the probe is situated to the outside of the nasal nari, and a second side is positioned to the inside of the nasal nari, and the tissue between the two sides is assessed by transillumination pulse oximetry.

Another object of the invention is to provide a novel configuration of an oximeter probe that is well-suited for placement on the tongue of a patient, in which one part of the probe is situated along one surface of the tongue, and an opposing part is positioned in such a manner as to capture a section of the tongue such that a transilluminable cross-section of tongue tissue is held between the two probe parts, and the tongue tissue between the two probe parts is assessed by transillumination pulse oximetry.

It is another object of the present invention to provide pulse oximeter probes dimensioned and configured to be expandable, spring-loaded, and flat surfaced for utilizing measurements on extremities and earlobes; bucal mucosal—bucal surface or dorsal ventral portion of the tongue; and properly sized configurations for the nasal alars (i.e., alar nares) and cheek and/or tongue for critically ill, burned, or traumatized patients. A related object is to provide a configuration for an oximeter probe that utilizes two opposed, substantially flat probe surfaces that tend toward each other, such as by spring tensioning.

It is a further object of the present invention to provide a monitoring system that measures vascular resistance and/or perfusion continuously to improve volume resuscitation and/or drug therapy.

It is still a further object of the present invention to provide a monitoring system that can be used as a multi-probe pulse oximeter to monitor blood oxygen saturation differences, pulse transit time differences, or blood pressure, or any combination thereof.

It is still another further object of the present invention to provide specifically constructed probes used to transmit and receive the light to vascular bed sites that are not normally available for use due to burns, trauma, and surgery on the extremity.

Still another object of the present invention to provide a monitoring system that is easily fabricated from low cost material and is adaptable for use in an operating room, intensive care unit, emergency room or other areas to treat patients in need of hemodynamic monitoring.

The foregoing has outlined some of the more pertinent objectives of the present invention. These objectives should be construed to be merely illustrative of some of the more prominent features and applications of the invention. Many other beneficial results can be attained by applying the disclosed invention in a different manner of modifying the invention as will be described.

It is to be understood that the foregoing general description and the following detailed description are exemplary and explanatory only and are not to be viewed as being restrictive of the present, as claimed. These and other objects, features and advantages of the present invention will become apparent after a review of the following detailed description of the disclosed embodiments and the appended claims.

BRIEF DESCRIPTION OF THE DRAWINGS

FIGS. 3A, B depicts a side view and a top view of a pulse oximeter probe for positioning on the tongue of a patient.

DETAILED DESCRIPTIONS OF EMBODIMENTS

The present invention discloses pulse oximeter probes for use with pulse oximeter systems in general. The present invention also discloses a novel non-invasive vascular perfusion and/or resistance status monitor apparatus and methods of using the same.

Figure 1:
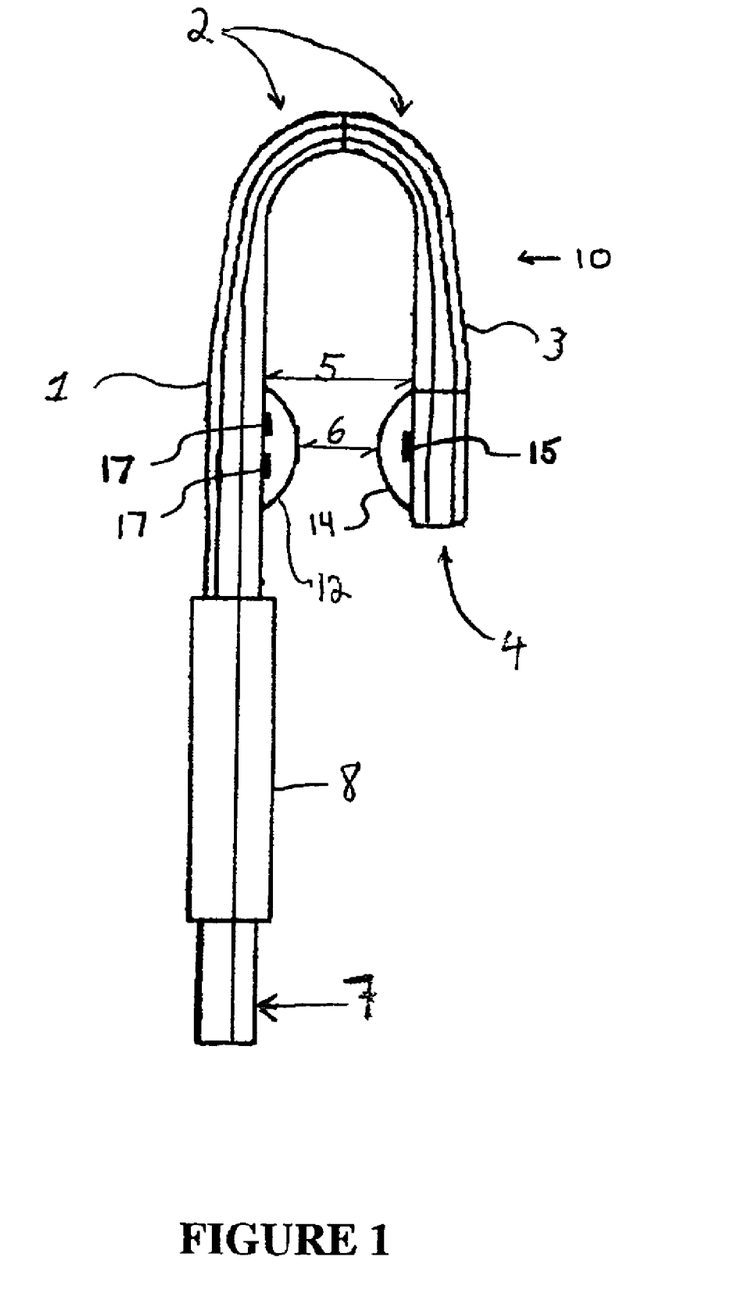
FIG. 1 illustrates a side view of a hook-shaped pulse oximeter probe showing a preferred positioning of a LED pad having two LED's and at least one photodiode detector according to the present invention. This probe is configured for positioning across the lip or cheek of a patient.

FIG. 1 illustrates a pulse oximeter probe, 10, of the invention, that is configured for placement with a section of the probe placed inside the mouth for measurement across the vascularized tissue of the lip or cheek. The probe, 10, as depicted in FIG. 1, is comprised of a frame that is generally hook-shaped, having a longer proximal arm, 1, a curved bridging section, 2, and a shorter distal arm, 3, the latter arm having a free end, 4, that enters the mouth when in use. At least one portion of the proximal arm, 1, is positioned at a specified distance, 5, from an opposing portion of the distal arm, 2, to provide a distance between the closest points of the two opposing arms, 6, that accommodates the thicknesses of the lips and/or cheeks of a desired range of patients. As shown in FIG. 1, the opposing portions of the proximal arm, 1, and the distal arm, 2, that are the specified distance, 5, represents most of the lengths of these arms. In other embodiments of this probe, a smaller percentage of the total span of opposing arm sections may be set to such specified distance.

The probe may be used once and disposed, or may be repeatedly used on different patients. Preferably, the probe frame is constructed of metals, plastics, and other materials subjectable to repeated cleaning with standard antiseptic solutions, or sterilizable by other means. A cable, 7, houses conductors (not shown), such as but not limited to insulated electrical wires, that connect operative components further in the probe, 10, with an oximeter monitor (not shown). A boot, 8, connects the cable, 7, to the proximal arm, 1, of the hook-shaped frame of the probe 10. Preferably the cable, 7, is flexible. The boot, 8, primarily serves to connect the cable, 7, with the frame, and secondarily to provide a handle with which the patient or attendant grip the probe. In other designs of the lip/cheek probe, a boot is not required where a direct connection is made between the cable and the frame of the probe.

In the embodiment depicted in FIG. 1, the probe 10 comprises two LEDs 17 within an LED pad, 12, and one photodiode detector 15 within a photodetector pad, 14. These are the operative components of the probe, 10, and are connected to a monitor system (not shown) by conductors (not shown) to transmit electrical signals.

Each probe 10 is sized appropriately to be placed with the open end, 4, inside a patient's mouth, so that the distance, 6, between the LED pad, 12, and the photodetector pad, 14, conforms to the thickness of the lip or cheek vascular bed of the patient. It is noted that FIG. 1 is not accurately drawn to scale, and given the true small size of the pads 12 and 14, the actual difference between the distances 5 and 6 is less than about 0.5 inches. In practice, one probe 10P (not shown) is sized for the average pediatric patient, age 6–12, and another probe 10A (not shown) is sized for the average adult patient.

The embodiment depicted in FIG. 1 has the light-sensing device, such as the photodiode detector, 15, positioned in the mouth, on the side with the open end, 4, as shown in FIG. 1. Having the light-sensing device on the inside side of the cheek or lip minimizes erroneous readings due to interference from ambient light sources. Such light sources are much more likely to affect a light-sensing source that is positioned on the outside side of the cheek or lip. However, having the light-sensing source positioned on the outside side of the cheek or lip is within the scope of the invention.

Individual conductors provide electrical signals that power the LEDs 17. Other conductors carry signals from the photodetector, 15. Optionally, other sensors, such as for temperature, may be added to the probe, 10, and have individual conductors for them also passing in the cable, 4, to the frame of the probe, 10. The probe, 10, is used to generate data used to calculate oxygen saturation, pulse shape, blood pressure measurement (by measurement of pulse transit time to a second site), and any combination of these.

The bridging section, 2, flexes to permit conformance to a range of tissue thicknesses greater than the nominal unflexed spans, as depicted by distances 5 and 6. The probe in FIG. 1 preferably is constructed of materials, such as nylon plastic, that impart a resiliency such that after bending, the probe returns substantially to its original shape. This resiliency allows the angular and dimensional relationships between the light-generating sources and the opposingly placed light detector to remain substantially consistent. Thus, the material for one embodiment of the probe has a degree of flexibility, and the material has sufficient memory to substantially return to its original shape after a normal flexion. This allows for standard use that may involve placement across lip and cheek tissue sections having different thicknesses, and movement across a thicker tissue section to ultimate placement at a thinner section.

For instance, in one embodiment of this configuration, the body of the probe, 10, is made of nylon plastic. The flexibility of the bridging section, 2, the proximal arm, 1, and the distal arm, 3, is such that less than 5 grams of force deflects the open end, 4, in one direction or the other (toward or away from the opposing section) by about 1/16 inch. The force required increases logarithmically, such that to move the open end, 4, outwardly 0.25 inch required between about 1,250 to 1,550 grams of force, and the force required to move the open end, 4, inwardly (toward the opposing section) required between about 2,200 to 2,700 grams of force. After such forces the nylon material demonstrated memory, returning to within 1/16 inch of the original position, thus demonstrating a resilient quality to the structure of the probe.

In addition, the material of each of the LED pad, 12, and the photodetector pad, 14, deflects upon application of pressure from adjacent tissue by up to about 0.050 inch. Thus, the overall flexibility is sufficient to accommodate a wide range of sizes of cheek and lip sections, which the axis of light transmission from the LEDs is reliably aligned to the photodiode or other light sensor. While not being bound to a particular theory, it is believed that maintaining appropriately narrow alignment of these elements improves the reliability, precision and accuracy of the signals from the probe.

More flexible probes are alternate embodiments of the present invention. For instance, the structural material and thickness is adjustable such that only between about 150 to 1,250 grams of force moves the open end, 4, outwardly 0.25 inch, and between about 200 to 2,200 grams of force the force moves the open end, 4, inwardly (toward the opposing section).

Less flexible probes also are alternate embodiments of the present invention. For instance, the structural material and thickness is adjustable such that between about 1,550 to 3,500 grams of force moves the open end, 4, outwardly 0.25 inch, and between about 2,700 to 5,000 grams of force the force moves the open end, 4, inwardly (toward the opposing section). Alternately, in a more rigid probe, the structural material and thickness is adjustable such that between about 3,500 to 5,500 grams of force moves the open end, 4, outwardly 0.25 inch, and between about 5,000 to 8,000 grams of force the force moves the open end, 4, inwardly (toward the opposing section). Such probes are made of metals or polymer composite materials. The resiliency is expected to vary inversely, roughly, with the flexibility of probes of such alternative embodiments.

Although in FIG. 1 the bridging section, 2, is curved, other embodiments of this lip/cheek probe may have a bridging section of any shape and angle, so long as it spans a distance and connects the opposing sides upon which the operative components of the probe are placed.

Figures 2A, 2B, 2C:
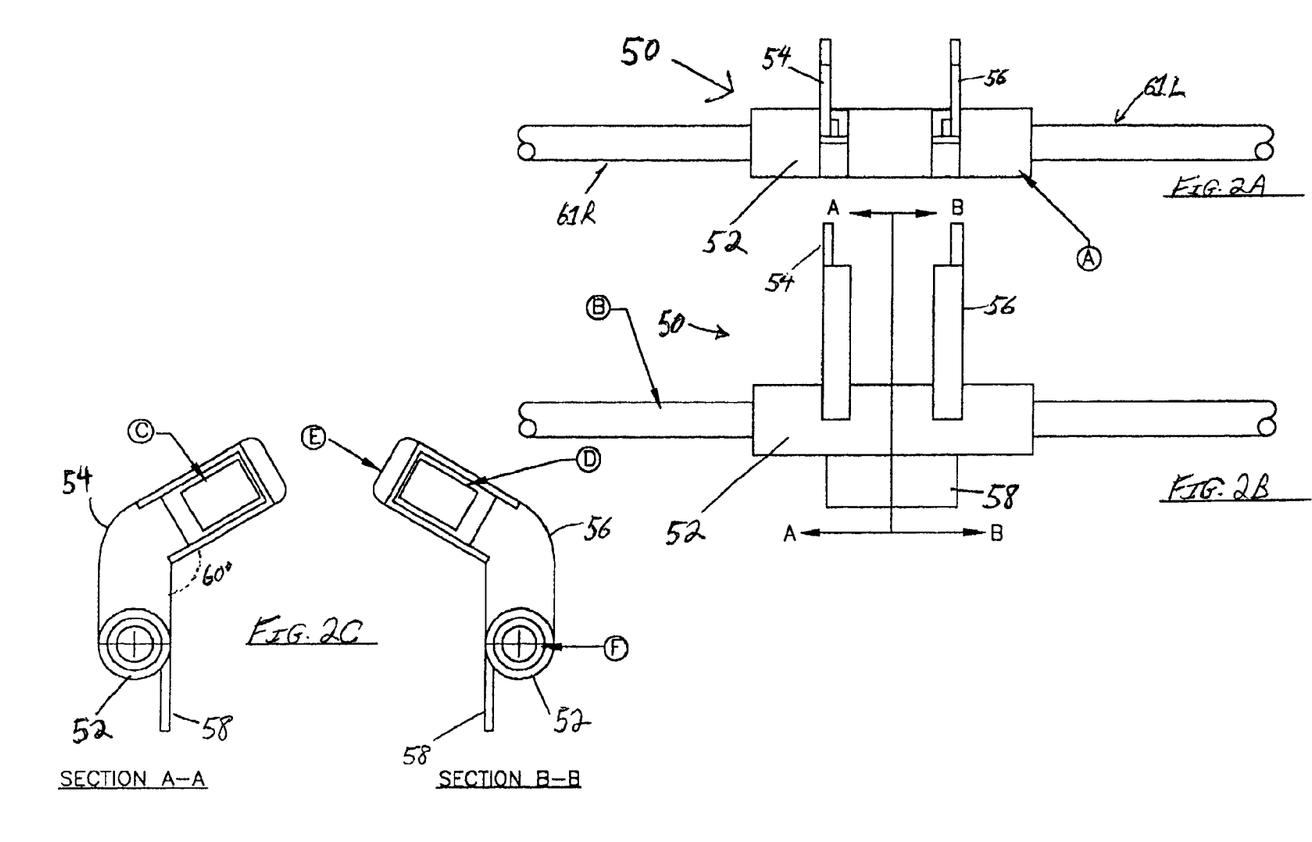
FIG. 2 provides a diagram of a pulse oximeter probe for positioning in the nares of a nose of a patient. Connecting wires are shown in schematic format.

FIGS. 2A–C illustrates a second pulse oximeter probe, 50, of the invention, that is configured for placement inside the nostrils of the nose for measurement across the vascularized tissue of the nasal septum. FIG. 2A is a top view, FIG. 2B is a side view, and FIG. 2C shows two cut-away views from a single mid-section line viewing opposite ends of the probe. From a resilient plastic housing, 52, extend two extensions, 54 and 56, that are sized to enter the nares of the nose in similar fashion to a nasal canula oxygen supply. These extensions, 54 and 56, are flattened in one dimension, as depicted in FIGS. 2A and 2B, and are angled at about 60 degrees in a second dimension, as shown in FIG. 2C.

Preferably, the two extensions, 54 and 56, are spaced apart from one another so as to fit snugly against the tissue of each side of the septum, to avoid interference from ambient lighting. Further, it has been learned that the area of the nasal septum closest to the face (e.g., the proximal area of the middle alar), is more consistently vascularized and thereby provides more consistent and reliable signals than the areas more distal, i.e., the septum closer to the point of the nose. For this reason, the two extensions, 54 and 56, are angled so that upon insertion and proper placement into position in the nostrils, the LEDs 62 and 64, located on extension 54, emit light directed through the preferred, proximal area of the nasal septum. In addition, a stabilizer, 58, embodied in FIG. 1 as a flat plate flush with and extending downward from the inside edge of the lower plane of the extensions 54 and 56 (before the extensions angle inward, see FIG. 2C), is designed to press against the area between the upper lip and nose to hold the desired position of the probe, 50, and in particular the LEDs 62 and 64, in relation to preferred, proximal area of the nasal septum. The stabilizer, 58, is in a preferred embodiment but is not a necessary component. Additional means of stabilizing the probe, 50, such as elastic straps from any part of the device that span the head of the patient, may be employed with or separately from the stabilizer, 58.

As for the probe described above in FIG. 1, timed electrical impulses from a pulse oximeter monitor system pass through two wires (not shown) in cables 61R and/or 61L to produce the light from LEDs 62 and 64. At least one photodetector, 66, is positioned on extension 56 to face and oppose LEDs 62 and 64 of extension 54. The photodetector 66, which typically is a light-sensing photodiode, detects changes in the light emitted by the LEDs 62 and 64 as that light is differentially absorbed between and during pulses across the capillaries of the septum tissue between the two extensions, 54 and 56. In one embodiment, LED 62 emits light around 650–670 nm, and LED 64 emits light around 880–940 nm. The electrical impulses are timed to be offset from one another. The photodetector, 66, detects the light passing through the septum of the nose, which is situated between extensions 54 and 56 when the probe 50 is in use. As discussed above, loss of signal through vascularized tissue such as the nasal septum is due both to background tissue absorption and the absorption by the blood in the arteries, which expands during a pulse. The signals from photodetector 66 pass through conductors (not shown) to the processor of the monitor system (not shown). Cables 61R and 61L preferably form a loop that may lie above the ears of the patient, and join to form a single cable (not shown). This single cable preferably terminates in an electrical plug suited for insertion into a matching socket in the pulse oximeter monitor system (not shown). In another preferred embodiment, the single cable terminates by connecting to an adapter cable, which in turn connects to a socket in the pulse oximeter monitor system (not shown). In a typical application, the signals from the light-sensing photodetector, 66, are ultimately received and processed by a general purpose computer or special purpose computer of the monitor system (not shown).

In a variation of the nasal probe, such as is exemplified in one embodiment in FIGS. 2A–C, oxygen is delivered with the same device that also measures trans-septum arterial oxygen saturation. In another variation, the pulse oximeter sensor is independent of an oxygen canula, and is a single-use unit. In yet another variation, the pulse oximeter sensor is independent of an oxygen canula, and is re-usable and readily cleanable with appropriate antiseptic cleaning agents. Other variations within the scope of the invention described and pictured can be developed by those of ordinary skill in the art.

Figure 3:
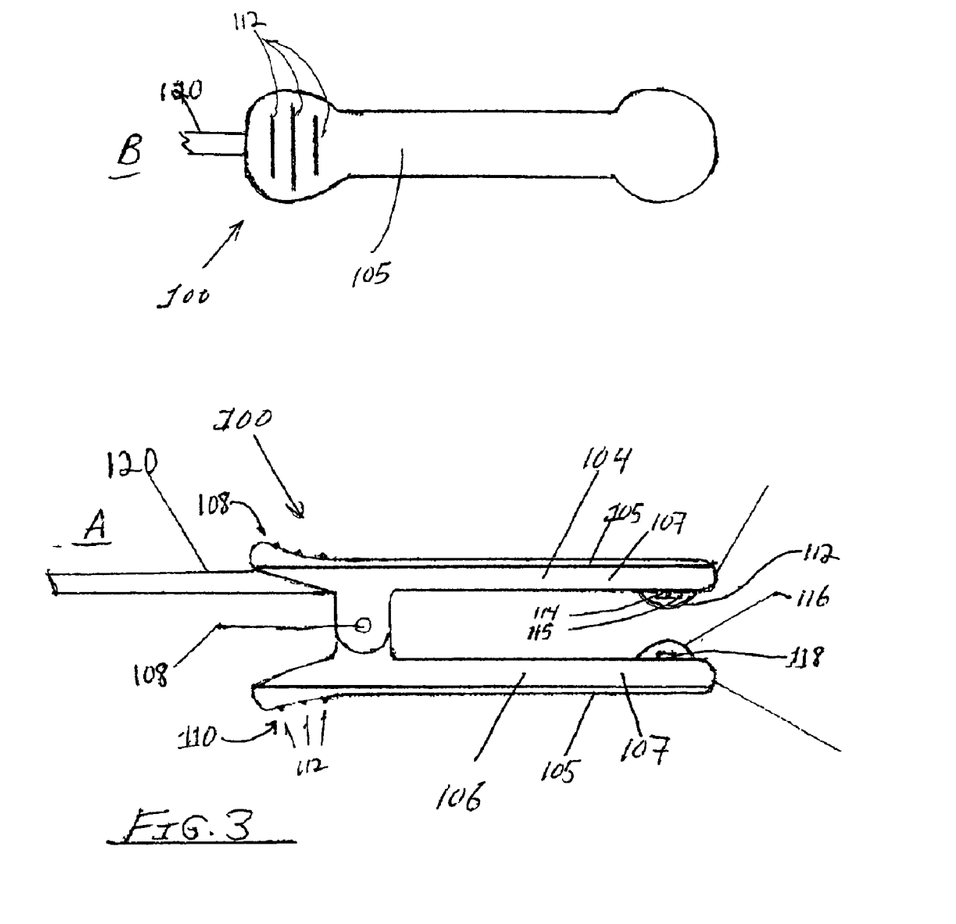

FIG. 3 illustrates a third pulse oximeter probe, 100, of the invention, that is configured for placement on the tongue of a patient for measurement across the vascularized tissue of the tongue. The probe, 100, has two substantially flat opposing arms, 104 and 106. A housing cover, 105, is joined with a housing base, 107, to form each of the two arms, 104 and 106. At one end of each of the two arms, 104 and 106, are finger pads, 108 and 110, which in the embodiment shown in FIG. 3 are on the housing covers, 105, and possess ridges, 112, to improve the grip.

The arms, 104 and 106, are tensioned to close against one another by a spring (not shown) which has a fulcrum at or near an axle, 108, that hingedly connects the two arms, 104 and 106, near one end. At or near the other end is an LED pad, 112, on one arm, 104. Within this pad, 112, are two light generating LEDs, 114 and 115. Opposite this housing, 112, on arm 106, is a photodetector pad, 116. Within this pad, 116, is at least one photodetector, 118. Electrical wire conductors (not shown) connect the LEDs, 114 and 115, and the photodetector, 118, to a pulse oximeter monitor system (not shown), via a cable, 120, passing from one end of the arm, 104. The inner surfaces of the arms, 104 and 106, in some variations of this probe are knobby or otherwise textured, especially around the LED pad, 112, and the photodetector pad, 116. This texturing is designed to better maintain a stable position of the probe, 100, on the tongue without use of excessive pressure of the spring.

The photodetector 118, which typically is a light-sensing photodiode, detects changes in the light emitted by the LEDs 114 and 115 as that light is differentially absorbed between and during pulses across the capillaries of the tongue tissue between the two arms, 104 and 106. In one embodiment, LED 114 emits light around 650–670 nm, and LED 115 emits light around 880–940 nm. The electrical impulses are timed to be offset from one another. The photodetector, 118, detects the light passing through the tongue which is situated between the first housing, 112, and the second housing, 116 of arms 104 and 106 when the probe 100 is in use. As discussed above, loss of signal through vascularized tissue such as the tongue is due both to background tissue absorption and the absorption by the blood in the arteries, which expands during a pulse. The signals from photodetector 118 pass through conductors (not shown) housed in cable 120 to the processor of the monitor system (not shown). Cable 120 preferably terminates in an electrical plug suited for insertion into a matching socket in the pulse oximeter monitor system (not shown). In another preferred embodiment, cable 120 terminates by connecting to an adapter cable, which in turn connects to a socket in the pulse oximeter monitor system (not shown). In a typical application, the signals from the light-sensing photodetector, 118, are ultimately received and processed by a general purpose computer or special purpose computer of the monitor system (not shown).

There are numerous means for hingedly joining the first arm and the second arm other than by an axle passing through the extensions of each arm (e.g., by axle 108). Other means include hinges of various materials and designs as known in the art, co-fabrication of the arms with a thinner section of flexible plastic between the two arms at one end, and pins, screws, and other fasteners as are known to those skilled in the art.

Similarly, means for tensioning the first arm and the second arm, so as to properly maintain tension on a section of the tongue of a patient, can be effectuated by means other than the spring described above. Separate elastic bands may be attached or may surround the arms, such as by attaching to protrusions spaced appropriately along the arms. Also, the natural flexibility and resilience of a co-fabricated structure comprising both arms connected by a section of resilient plastic can provide both the means for hinging and the means for tensioning. Such fabrications may be deemed suitable for disposable units.

It is noted that for this and other probes disclosed herein, a single source generating at least two different light frequencies may be utilized instead of LEDs. Alternately, more than two LEDs may be used, such as to generate light at more than two frequency bands, for instance to increase accuracy and/or detect other forms of hemoglobin. Also, light receiving sensors, or photodetectors, other than photodiodes may be used, and more than one such sensor may be used in a single probe.

The pulse oximeter probes 10, 50, and 100 as depicted and as used in the monitoring system in the present invention take measurements by transillumination, as opposed to reflectance. This is the preferred configuration. However, for any of these probes, both the light-generating devices, and the photodetector devices, can be configured adjacent to one another, on one arm or extension, to measure reflectance of the tissue on the interior of the mouth (e.g., the cheek), the lip, the nasal septum, or the tongue.

Figure 4:
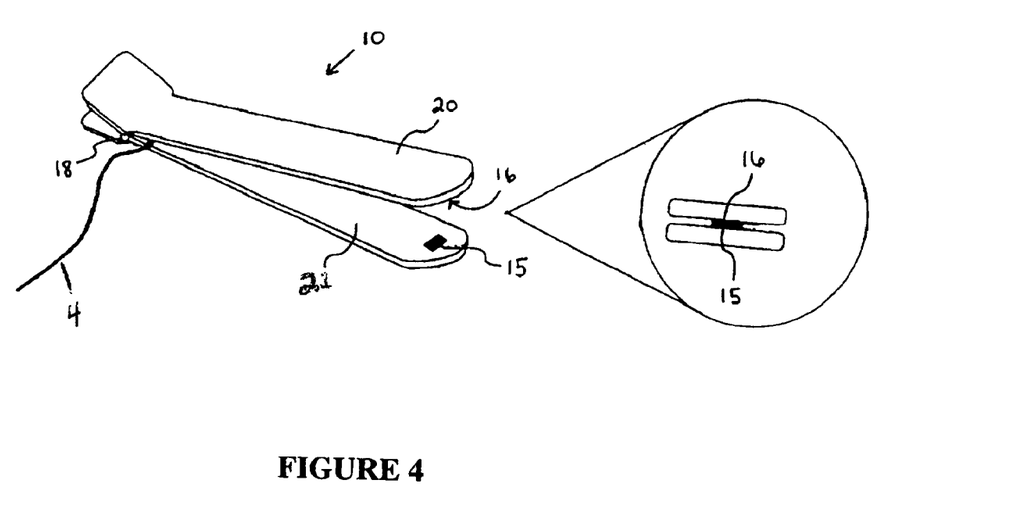
FIG. 4 illustrates a perspective angled side view and an exploded frontal cross-sectional side view of a flat surfaced, elongated spring-loaded pulse oximeter probe showing the configuration of the LED's and the photodiode detector according to the present invention.

FIG. 4 depicts another general configuration of an oximeter probe of the present invention. This probe 10 can be dimensioned and configured to be expandable and tensioned to close by a spring, 18. Near the distal, operative end of one substantially flattened side, 20, is an LED array, 16, and opposing it near the distal, operative end of the opposing substantially flattened side, 21, is a light detecting sensor, preferably a photodiode, 15. A cable, 4, connects the LED array, 16, and light detecting sensor to a pulse oximeter monitor system (shown in the magnified end view)). This pulse oximetry probe can be used to measure pulse-based differences in light absorbence across vascularized tissue of a patient in a number of locations, including but not limited to the cheek, the lip, the nasal alars (alar nari), the nasal septum, fingers, and toes.

By "substantially flattened" is meant that the height of the structure of the side is small relative to the greater of the length or width of that side. Preferably the ratio of the height to the greater of the length or width of "substantially flattened" side is between about 0.2:1 and 0.001:1, more preferably this ratio is between about 0.02:1 and 0.005:1, and yet more preferably this ratio is between about 0.01:1 and 0.005:1. For greater applicability to typical physical requirements in use, each side also is substantially longer than wide. By "substantially longer than wide" is meant that the width of the structure of the side is small relative to the length of that side. Preferably the ratio of the width to the length a side described as "substantially longer than wide" is between about 0.7:1 and 0.02:1, more preferably this ratio is between about 0.025:1 and 0.05:1, and yet more preferably this ratio is between about 0.025:1 and 0.1:1.

Also, it is noted that in place of the spring, 18, any hinging means as known in the art can be used. Such hinging means may include a raised section along or separate from the sides, such that a fixed space is created at the point of the hinging means. This would obviate the need for a bend in the sides at the spring, 18, as shown in FIG. 4 (which is required in FIG. 4 to lever open the operative ends). These substantially flattened probes are configured such that the inner faces of both sides substantially oppose each other and, based on the spacing and configuration of the hinging means, are sufficiently separable to widen to encompass a desired tissue to be monitored for blood oxygen saturation between the light emitting structure and the light detecting structure at the operative end. It is noted that these structure may each be enclosed in a pad, or may not be so enclosed. As for other probes disclosed herein, a monitoring system connected to the probe modulates light signal production and receives signals of light detected by at least one light-detecting structure positioned at the operative end of one of the sides, such as 20 or 21 in FIG. 4.

Figure 5:
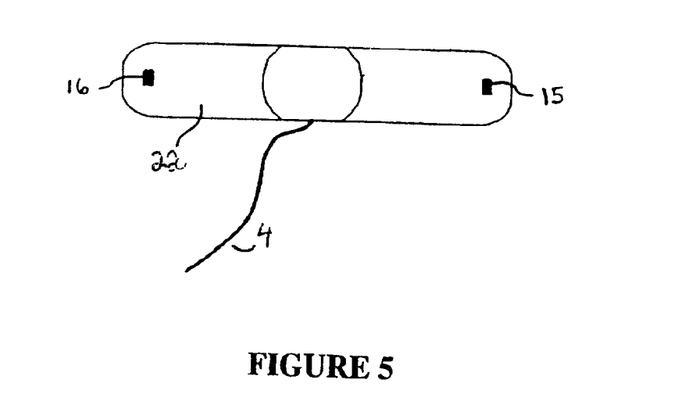
FIG. 5 illustrates an internal view of the pulse oximeter sheath according to the present invention.
Figure 6:
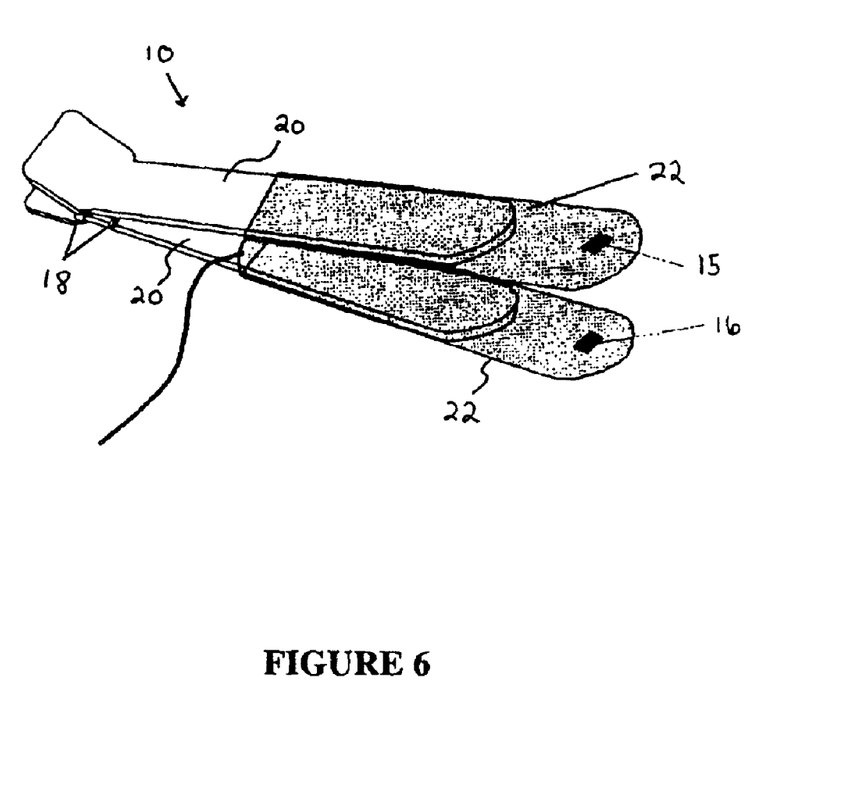
FIG. 6 illustrates a perspective angled side view of a flat surfaced, elongated spring-loaded pulse oximeter probe showing the features of the pulse oximeter sheath according to the present invention.

Also, the above substantially flattened sides with hinging means may be produced without light-emitting and light-detecting structures, and sleeves, such as described below, bearing such structures, would then be slipped over the sides to yield an operable oximeter probe. For instance, as shown in FIGS. 5 and 6, a probe 10 with a flat surface 20 is suitable for to receive a flexible sleeve, 22, that bears an LED array, 16, and light detecting sensor, preferably a photodiode, 15. This slips over the flat-surfaced structure, as shown about halfway on in FIG. 6. As for the probe in FIG. 4, a cable, 4, connects the LED array, 16, and light detecting sensor to a pulse oximeter monitor system (not shown).

In operation, the devices depicted in FIGS. 4–6 are placed around a finger, earlobe, or other extremity in order to obtain data.

Thus, another aspect of the present invention is a disposable sleeve that fits over any of the pulse oximeter probes disclosed and claimed herein, and over conventional probes. A sleeve is constructed of a flexible material, and is relatively thin, in the general range of 0.005 to 0.050 inches thick, more preferably in the range of 0.010 to 0.025 inches thick, and most preferably in the range of 0.010 to 0.015 inches thick. The sleeve is manufactured to slide over the major structural features of the probe to provide a barrier to reduce the chance of contamination from one patient to a second patient using the same probe. An example of such sleeve is shown in FIG. 5, and its implementation over a probe is shown in FIG. 6. In this case the sleeve is constructed to include the light generating and the light sensing features, and associated conductors. However, in other embodiments of the sleeve, such features are on the major structural features, whether frames, arms, etc., and the sleeve slides over such features, and at least in the areas of such light producing and light sensing features the sleeve is highly transparent to the critical wavelengths used by the pulse oximeter. The sleeves cover both arms, or extensions, of probes having two distinct arms. Preferably a continuously integral section of the sleeve joins the sleeve sections that cover both arms or extensions of the probe, in order to, inter alia, protect the intervening parts of the probe. For a probe such as the probe of FIG. 1, the sleeve is configured to the shape of the probe and slides over starting at the end, 4, of the arm, 3, and covers up to, and preferably including, the boot, 8.

In some sleeve embodiments, a stretchable aspect of one or more parts, or of the entire sleeve, stretches over a protuberance or other prominence at one or more parts of the major structural features over which the sleeve is sliding, and improves the fit of the sleeve. This also better assures that the sleeve does not slide off the probe during normal uses. Alternate means to secure the sleeve onto the probe such as are known to those of skill in the art may be used. The sleeves themselves can be disposable; however, the sleeves also can be made of easily sterilizable materials and be sterilized between uses.

The probes and the sleeve covers of the present invention are supplied as clean or as sterile, depending on the needs of the end user and the budgetary constraints of the end user. Clean but not sterile probes and sleeves will be less expensive, and may be suitable for many applications. Where there is an elevated risk of major harm from an infection, for instance in immunocompromised patients undergoing transplants with immunosuppressive drugs or undergoing chemotherapy, sterile probes would be more appropriate than merely clean probes. Many configurations of the probes are cleanable using alcohol and/or detergent/disinfectant solutions, and other configurations are disposable.

All of the above disclosed probes operate in a typical manner of a pulse oximeter, as described herein and in articles and patents cited and incorporated by reference. Each LED emits its specific frequency hundreds of times per second, and the absorption (or transmittance) readings by a sensor, such as a photodiode, are transmitted to a computer. There a software system performs averaging (optionally deleting outliers), and by differences in wavelengths' absorption or transmittance at the pulse peaks, determines arterial oxygen saturation. In a standard two-LED system, this is done by an algorithm that calculates the ratio of the peak absorbence at 650–670 nm divided by the base absorbence at this wavelength range, and compares this ratio to the peak absorbence at 880–940 nm to the base absorbence at the 880–940 nm range. The base absorbence reflects the non-pulse background absorbence by tissues other than the artery at maximum width during the pulse. This calculation provides an estimate of arterial oxygen saturation. A graph of the pulse surge, or shape, over time, also can be obtained.

All of the above-disclosed probes are expected to have significant use in the intensive care units, operating rooms, post-surgery recovery rooms, and in ambulance related situations where a patient in need of monitoring has few suitable monitoring sites. The size and shape of each probe will depend on whether the patient is an adult or child.

When two or more probes are used together, data from multiple probes is processed to provide continuous and simultaneous cross-site comparisons of the arterial blood oxygen saturation status at and comparisons between two or more tissue sites (and, as desired, blood pressure estimates based on transit time differences and/or other related parameters). The monitoring system receiving these signals includes at least one program containing computer software (not shown) comprising instructions which causes the computer processor to receive and calculate various oxygen saturation values. Optionally, the monitoring system may receive signals from separate probes or sensors to assess blood pressure values, which optionally may be compared (either simultaneously or separately) with blood pressure estimates based on signals received from each of the probes determining arterial blood oxygen saturation and vascular perfusion/resistance of a patient. Depending upon the software used, and the addition of separate blood pressure probes or sensors, the monitor may be used as a dual pulse oximeter, a saturation difference monitor, a transit time monitor, a periodic blood pressure monitor, or a noninvasive continuous blood pressure monitor. Specific examples are provided below that demonstrate a non-exclusive range of applications for the monitoring system which compares signals from a central source site (CSS) with signals from at least one advantageously positioned peripheral site (PS), as those terms are defined herein.

Figure 7:
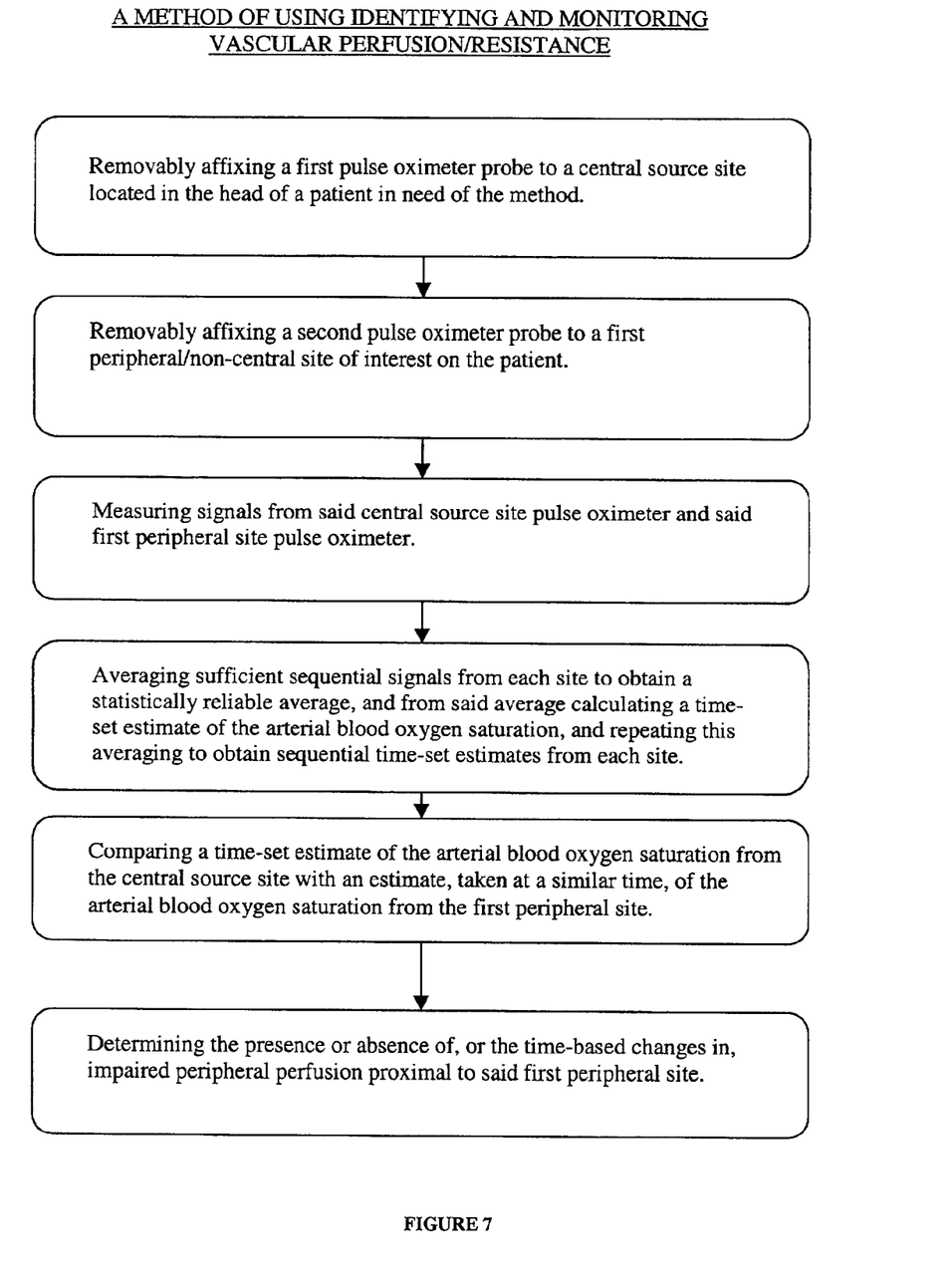
FIG. 7 is a flow chart showing one method utilized by the non-invasive vascular perfusion/resistance monitoring system to measure oxygen saturation values according to the present invention.

FIG. 7 depicts the steps of a basic method using the monitor system that includes one probe positioned in a CSS, and one probe in a PS. A first pulse oximeter probe is removably affixed to a CSS in the head of the patient. This is most preferably any of the specially configured probes, or could be a conventional probe. A second pulse oximeter probe is removably affixed to a PS such as a finger or a toe. This can be any of the specially configured probes, or a conventional probe. The monitoring system is started, the LEDs or other light generating sources in the probes emit designated light at designated frequencies and periodicities, and signals from the CSS and from the PS are measured and transmitted to the monitoring system computer. Here, adjacent signals of the same type (wavelength and probe) are averaged to obtain a statistically reliable average. As appropriate based on the software program, certain outliers as may be caused by movement of the patient, light contamination from an outside source, etc., are eliminated from consideration. The averaging is repeated and the averaged values are compared based on the time sequencing of the respective averages. That is, average values from a specific time from the CSS probe are compared to average values from the same time span from the PS probe. The software calculates arterial blood oxygen saturation percentages based on the differential absorption of the different species of hemoglobin, and percent oxygen saturation at the CSS and the PS are compared. Based on criteria input into the monitoring system and reflected in the software's calculations, the presence or absence of impaired peripheral perfusion are shown as an output reading of the monitoring system. Alternatively, if impaired perfusion has already been established, the tracking of time-based changes in the saturation differences between the CSS and the PS are read out or charted.

The method shown in FIG. 7 is conducted with an apparatus having the stated functional capabilities. Also, an oximeter monitoring system has the basic physical components that perform the required centralized functions, and which is attached to at least two oximeter probes to perform the above-described method.

Further, a variation of the method of FIG. 7 is to have an additional PS probe, and compare not only the first PS probe to the CSS probe, but to also compare the first and second PS probes' signals to one another. This can, for instance, demonstrate impaired peripheral perfusion in one body area, but not in another body area or extremity.

The apparatuses, methods and systems of the present invention can be applied to both humans and animals, i.e., to living vertebrate organisms. Its application in human medicine (adult & pediatrics) would significantly improve the estimation of vascular perfusion or resistance by pulse oximetry; however, veterinary medicine also would greatly benefit from its use. This superior monitoring system would utilize at least two pulse oximeter probes, one of which is designed for use with a highly perfused central tissue, such as a lip, tongue, nares, cheek; and the other probe is designed for use to less perfused areas such as peripheral tissues, or any combination thereof.

The following specific examples are meant to be demonstrative, but not limiting, of the possible applications of the present invention.

EXAMPLE 1

Data from a small number of volunteer subjects was obtained. This data provided preliminary support for the hypothesis that differences in CSS and PS estimates of arterial blood oxygen saturation levels can provide diagnostic information about the status of peripheral blood circulation. These data are summarized below.

All sets of data were taken three times, except that data for subjects 1 and 9 were only taken two times (duplicate data sets). Subjects 1–3 had no history of chronic obstructive pulmonary disease or other conditions that would be expected to cause lowered peripheral circulation. Except for one reading of 93% for subject 1, all estimates of arterial oxygen saturation were 95% or higher, and the PS (a finger, using a standard commercial probe) readings were within two percentage points of either CSS sites (lip and cheek). For the data set in which subject 1's cheek probe reading was 93%, the lip reading was 98% and the finger reading was 96%. Overall, the data of subjects 1–3 suggest that in a healthy subject the CSS and PS readings taken at or near the same time will be relatively close, within about 5 percentage points or less, and all of the readings will be high.

Subject 4 had average readings at the PS finger site of 89%, and at the CSS cheek site, 88.7%, so these sites has essentially identical estimates. No signal was recorded at the lip CSS. Although there was no difference between the CSS cheek and the PS readings, the oxygen estimate was low and indicated a generalized problem.

Subject 5 had a PS average of 85%; the lip CSS average was 88.3%, and the cheek CSS average was 91.3%. The absolute levels are low, and the difference between CSS and PS values ranges from about 3 for the lip to about 6 for the cheek. This appears to suggest a peripheral circulation problem, and the low absolute levels indicate a generalized problem with oxygenation. This subject was known to have COPD.

Subjects 6–8 were known to have COPD. The average values for finger, lip and cheek were 85, 90, and 89, respectively for Subject 6. The 4–5% less percent saturation for the peripheral site supports the present hypothesis. Subject 7's finger data varied between 77–80% during the readings, and is considered unreliable. One of subject 8's data points for the finger was 79%, whereas the other two were 85%. This suggests that the 79% reading is erroneous. Disregarding this data point, Subject 8 had 85%, 87.3%, and 85.6% averages for the finger, lip and cheek sites, respectively. Here, all readings are fairly close, and the absolute values are alarmingly low. The data from this subject do not support the hypothesis; however the circulation for this subject may not be impaired peripherally. Further investigation can resolve this and other points.

Regarding the latter, subject 11's data was anomalous in that the finger site averaged 93.3%, whereas the lip and cheek sites averaged 90.7% and 86.7%, respectively. The reason for this is unknown; the data could be spurious or could indicate unusual circulation in a small percentage of the population. Individual differences in circulatory systems (based in part on genetics, and in part on non-genetically based embryological development, and on physical conditioning) may form the basis for such anomalies in a percentage of the population. Highly variable and incomplete data for Subjects 9 and 10 were considered to render the value of their data questionable, and those data were not analyzed.

Thus, this preliminary data provided some indication of differences between CSS and PS and differences between normal and circulation-compromised subjects. The data also supported the need to investigate broader populations with known circulatory conditions to develop more predictive guidelines for the probe data differences. Even with the limited data of this example, it is apparent that the comparison of CSS and PS sites can provide a useful assessment of the state of the circulatory system even where there is no major difference, and there is not a disease state presenting itself. That is, such results of roughly equivalent CSS and PS data at a high oxygen saturation level would support a conclusion that the peripheral circulation is not impaired.

EXAMPLE 2

An elderly patient with relatively advanced diabetes comes in for monitoring of the status of perfusion in the right leg, which is diagnosed with severe atherosclerosis and related impaired vascular perfusion. A monitor of the present invention is utilized, with one CSS probe measuring signals across the nasal septum, and a PS probe on the large toe of the right foot. A new medication is started, and ongoing weekly data from the monitor tracks the changes in perfusion in the right leg by comparing oxygen saturation values of the CSS probe with the values of the PS probe. Such data indicates the degree of effectiveness of the new medication.

EXAMPLE 3

A critically burned patient is brought into an emergency room. As vital signs and assessment is taking place, a pulse oximeter probe as shown in FIG. 1 is placed into the patient's mouth to read cheek tissue as a central site source, and a pulse oximeter probe as shown in FIG. 4 is placed at each of the patient's large toes. Within less than one minute, the monitor of the present invention indicates below normal blood perfusion in the right leg, based on the signals from the probe placed on the right toe, compared to the central source site and the left toe probe. A probe is placed on a right finger, and this provides comparable data to the left toe. The attending physician is able to surmise that an injury or disease condition is adversely affecting perfusion in the right leg, orders more detailed testing, and increases the percent oxygen on the respirator to counter the low oxygen in the affected leg. The monitoring system tracks changes in the oxygen saturation values of blood in the right toe as this initial treatment has an effect.

EXAMPLE 4

A patient suspected of having Chronic Pulmonary Obstructive Disease is admitted to an emergency room with breathing difficulties. The patient also reports pain in both legs after involved in a minor traffic accident, which is the immediate cause of admission. Minor bruising is apparent on the front of the left leg. Along with other tests and monitoring, a pulse oximeter monitor of the present invention is utilized, with on CSS probe on the nares of the nose, and a PS probe on the large toe of each of both feet. Alarmingly, the CSS probe estimates that the arterial oxygen saturation at the CSS site is below about 85 percent, indicating hypoxia. The pulse oximeter monitor in both PS sites estimates even lower oxygen saturation, by about 5 percent, compared to the CSS site. There is no response to bronchodilator therapy, and the chest x-ray shows moderate fibrosis, and no attenuated vessels or hyperinflation. The initial diagnosis, aided by the pulse oximetry data, is bronchial COPD. Oxygen therapy is provided, and the pulse oximetry data is utilized to monitor increases in blood oxygen saturation both at the CSS and PS sites.

Preferably, the oximeter probes and sleeves are easily fabricated from low cost materials and are adaptable for use in an operating room, intensive care unit, emergency department, post-surgery recovery areas and other areas to treat patients in need of hemodynamic monitoring. The monitoring system is particularly applicable for use with patients in whom hypotension or poor perfusion are problematic. In addition, the monitoring system is particularly well suited for use with multi-trauma and thermally injured patients who either have severe peripheral vasoconstriction or have severely damaged or destroyed peripheral vascular beds. Through combining at least two pulse oximeters capable of measuring desired parameters at at least two locations into a single monitor system, the present invention provides a more accurate assessment of perfusion and resistance in patients, than any of the presently available single probe pulse oximeters.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for analyzing pulse oximeter probe signals from at least two sites on a living vertebrate to determine the presence or absence of, or to monitor changes in, impaired peripheral perfusion, comprising the steps of:
   a. removably affixing a first pulse oximeter probe to a central source site located in the head of a patient in need of said method;
   b. removably affixing a second pulse oximeter probe to a first peripheral site of interest on said patient;
   c. measuring signals from said central source site pulse oximeter and said first peripheral site pulse oximeter;
   d. averaging sufficient sequential signals from each site to obtain a statistically reliable average, and from said average calculating a time-set estimate of the arterial blood oxygen saturation, and repeating this averaging to obtain sequential time-set estimates from each site;
   e. comparing a time-set estimate of the arterial blood oxygen saturation from the central source site with an estimate, taken at a similar time, of the arterial blood oxygen saturation from the first peripheral site; and
   f. determining the presence or absence of, or the time-based changes in, impaired peripheral perfusion proximal to said first peripheral site.

2. The method of claim 1 wherein said central source site is selected from the group consisting of cheek, nasal septum, alar nares, and tongue.

3. The method of claim 1 wherein said first peripheral site is selected from the group consisting of a finger, a toe, and a section of tissue distal from an area of potential damage or disease adversely affecting, suspected or known to have compromised the peripheral vascular resistance and/or peripheral blood perfusion, and/or peripheral vascular disease.

4. The method of claim 1 wherein said monitoring assesses changes over time in oxygenation of tissues proximal to said second pulse oximeter during drug dosing/effectiveness and/or reoxygenation procedures.

5. The method of claim 1, additionally comprising estimating the blood pressure of said living vertebrate through analysis of pulse time delay of said signals between said at least two sites.

6. The method of claim 5, additionally comprising comparing the analysis of said pulse time delay with blood pressure estimates obtained by other means, and applying a factor to enhance the accuracy of said estimating the blood pressure.

7. The method of claim 1, wherein said presence of impaired peripheral perfusion is related to decreased peripheral circulation caused by a condition selected from the group consisting of atherosclerosis, Raynaud's disease, Buerger's disease, chronic obstructive pulmonary disease, embolic occlusive disease, and progressive diabetes.

8. The method of claim 1, wherein said presence of impaired peripheral perfusion is related to lower circulation to the limbs of said living vertebrate, caused by an acute condition selected from the group consisting of shock, trauma, and mechanical injury.

9. Apparatus for analyzing pulse oximeter probe signals from at least two sites on a living vertebrate, to determine the presence or absence of, or to monitor changes in, impaired peripheral perfusion, comprising:
   a. means for receiving pulse oximeter probe signals from at least two sites on a living vertebrate, wherein at least one said site is a central source site and at least one said site is a peripheral site;
   b. means for signal averaging sufficient signals from each pulse oximeter probe site to obtain a statistically reliable average;
   c. means for calculating a time-set estimate of the arterial blood oxygen saturation based on said statistically reliable average;
   d. means for obtaining sequential time-set estimates of arterial blood oxygen saturation from each site;
   e. means for comparing a time-set estimate of the arterial blood oxygen saturation from the central source site with an estimate, taken at a similar time, of the arterial blood oxygen saturation from the first peripheral site;
   f. means for determining the presence or absence of, or the time-based changes in, impaired peripheral perfusion proximal to said first peripheral site based on the extent to which said first peripheral site has lower oxygen saturation than said central source site; and
   g. means for presenting results to a user of said apparatus.

10. The apparatus of claim 9, additionally comprising means for estimating blood pressure through analysis of pulse time delay between said at least two sites.

11. An oximeter monitor system for analyzing pulse oximeter probe signals from at least two sites on a living vertebrate, to determine the presence or absence of, or to monitor changes in, impaired peripheral perfusion, comprising:
  a. output circuitry to deliver timed signals to energize light generating components of a least two pulse oximeter probes;
  b. input circuitry to receive signals from said at least two pulse oximeter probes positioned at at least two sites on a living vertebrate, wherein at least one said site is a central source site and at least one said site is a peripheral site;
  c. a computer loaded with software to
    1. provide timed signals to energize said light generating components;
    2. average sufficient signals from each pulse oximeter probe site to obtain a statistically reliable average;
    3. calculate a time-set estimate of the arterial blood oxygen saturation based on said statistically reliable average;
    4. repeat steps 2 and 3 to obtain sequential time-set estimates of arterial blood oxygen saturation from each site;
    5. compare a time-set estimate of the arterial blood oxygen saturation from the central source site with an estimate, taken at a similar time, of the arterial blood oxygen saturation from the first peripheral site; and
    6. based on developed parameters, determine the presence or absence of, or the time-based changes in, impaired peripheral perfusion proximal to said first peripheral site based on the extent to which said first peripheral site has lower oxygen saturation than said central souree site; and
  d. a read-out device to provide results to a user of said system.

12. The oximeter monitor system of claim 11, additionally comprising software in said computer with steps for estimating blood pressure through analysis of pulse time delay between said at least two sites, including means for adjustment of blood pressure estimates based on at least one comparison with a result from a conventional blood pressure measurement of said living vertebrate.

* * * * *

UNITED STATES PATENT AND TRADEMARK OFFICE
CERTIFICATE OF CORRECTION

PATENT NO. : 6,909,912 B2  
APPLICATION NO. : 10/176310  
DATED : June 21, 2005  
INVENTOR(S) : Richard Melker

Page 1 of 1

It is certified that error appears in the above-identified patent and that said Letters Patent is hereby corrected as shown below:

On the title page item (73), delete: Beta Biomed, Inc., Rowlett, TX (US)

Signed and Sealed this

Eleventh Day of September, 2007

JON W. DUDAS  
*Director of the United States Patent and Trademark Office*